(12) United States Patent
Park

(10) Patent No.: US 10,827,774 B2
(45) Date of Patent: Nov. 10, 2020

(54) METHOD FOR PREPARING FOOD CONTAINING MEDICINAL HERB EXTRACTS BENEFICIAL FOR LIVER AND FOOD PREPARED THEREBY

(71) Applicant: Dal Soo Park, Pocheon-si (KR)

(72) Inventor: Dal Soo Park, Pocheon-si (KR)

( * ) Notice: Subject to any disclaimer, the term of this patent is extended or adjusted under 35 U.S.C. 154(b) by 27 days.

(21) Appl. No.: 16/314,077

(22) PCT Filed: Jul. 17, 2017

(86) PCT No.: PCT/KR2017/007655
§ 371 (c)(1),
(2) Date: Dec. 28, 2018

(87) PCT Pub. No.: WO2018/016822
PCT Pub. Date: Jan. 25, 2018

(65) Prior Publication Data
US 2019/0200661 A1    Jul. 4, 2019

(30) Foreign Application Priority Data
Jul. 18, 2016 (KR) ........................ 10-2016-0091027

(51) Int. Cl.
| | |
|---|---|
| A23L 33/105 | (2016.01) |
| B01D 11/02 | (2006.01) |
| A23L 3/30 | (2006.01) |
| A61K 36/72 | (2006.01) |
| A61K 36/282 | (2006.01) |
| A61K 36/488 | (2006.01) |
| A61K 36/232 | (2006.01) |
| A61K 36/484 | (2006.01) |
| A61K 36/54 | (2006.01) |
| A61K 36/9066 | (2006.01) |
| A23L 33/115 | (2016.01) |

(52) U.S. Cl.
CPC .............. *A23L 33/105* (2016.08); *A23L 3/30* (2013.01); *A61K 36/232* (2013.01); *A61K 36/282* (2013.01); *A61K 36/484* (2013.01); *A61K 36/488* (2013.01); *A61K 36/54* (2013.01); *A61K 36/72* (2013.01); *A61K 36/9066* (2013.01); *B01D 11/0288* (2013.01); *A23L 33/115* (2016.08); *A23V 2002/00* (2013.01); *A61K 2236/13* (2013.01); *A61K 2236/331* (2013.01); *A61K 2236/53* (2013.01); *B01D 11/0284* (2013.01)

(58) Field of Classification Search
None
See application file for complete search history.

(56) References Cited

FOREIGN PATENT DOCUMENTS

| | | |
|---|---|---|
| KR | 10-2002-0079854 A | 12/2002 |
| KR | 10-2003-0027615 A | 4/2003 |
| KR | 10-0403721 B1 | 11/2003 |
| KR | 10-2011-0112925 A | 10/2011 |
| KR | 10-1106499 B1 | 1/2012 |
| KR | 10-2013-0088704 A | 7/2013 |
| KR | 10-2014-0043176 A | 4/2014 |
| KR | 10-2015-0087715 A | 7/2015 |
| KR | 10-2015-0098525 A | 8/2015 |
| KR | 10-1728986 B1 | 4/2017 |

OTHER PUBLICATIONS

English translation of KR 10-2011-0112925—2011.*
International Search Report for PCT/KR2017/007655 dated Oct. 25, 2017.

* cited by examiner

*Primary Examiner* — Susan Hoffman
(74) *Attorney, Agent, or Firm* — Hauptman Ham, LLP

(57) ABSTRACT

Described herein is method of preparing a food including medicinal herb extracts for strengthening liver function. The method includes washing medicinal herbs, extracting the medicinal herbs to obtain extracts, passing the extracts through a packed column, aging and filtering the extracts, mixing the filtered extracts with palm oil and grape seeds to obtain a mixture, aging the mixture, sterilizing the aged mixture, passing the sterilizing mixture through a packed column, packaging the sterilized mixture, and making the packaged mixture into a final product. The medicinal herbs includes *Hovenia dulcis*, young leaves of *Artemisia scoparia*, *Pueraria thunbergiana*, *Curcuma longa*, *Angelica gigas*, licorice, or cinnamon. Also described herein is the food including medicinal herb extracts for strengthening liver function made according to the method.

2 Claims, 1 Drawing Sheet

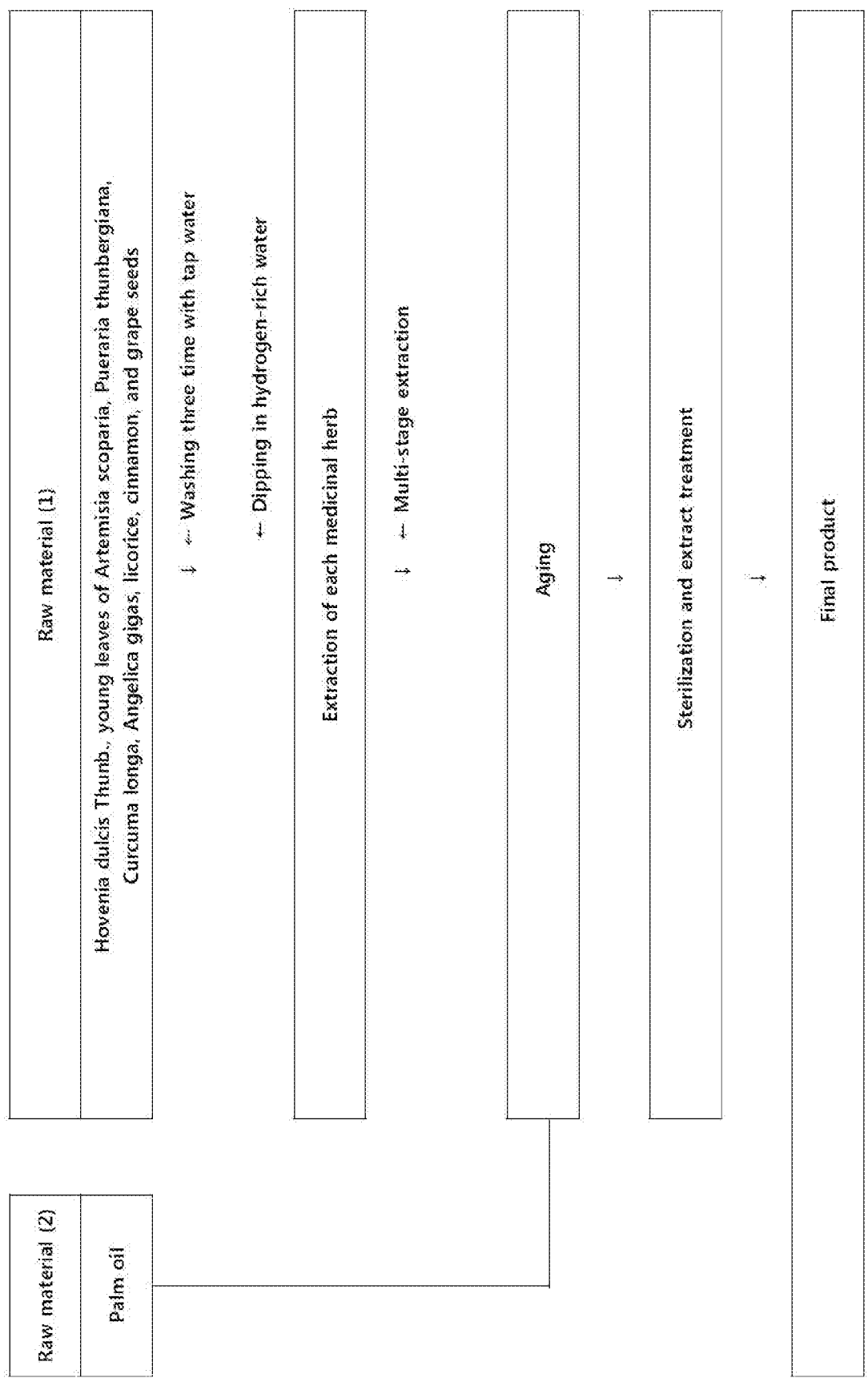

METHOD FOR PREPARING FOOD CONTAINING MEDICINAL HERB EXTRACTS BENEFICIAL FOR LIVER AND FOOD PREPARED THEREBY

BACKGROUND OF THE INVENTION

Field of the Invention

The present invention relates to a method of preparing a food containing medicinal herb extracts beneficial for the liver from medicinal herbs and palm oil and a food prepared thereby. More specifically, the present invention relates to a method of preparing a food containing medicinal herb extracts beneficial for the liver from the medicinal herbs and palm oil having various functionalities and pharmacological actions, the method comprising: washing and dipping medicinal herbs, including *Hovenia dulcis* Thunb., young leaves of *Artemisia scoparia, Pueraria thunbergiana, Curcuma longa, Angelica gigas*, licorice, and cinnamon; subjecting the dipped medicinal herbs to multi-stage extraction; aging the extracts at low temperature; and mixing the aged extracts with palm oil and grape seed oil, and to a food prepared thereby.

Description of the Prior Art

Prior art documents related to liver strengthening include: Korean Patent No. 10-1106499, entitled "Food composition for liver protection containing young branches of *Hovenia dulcis* Thunb."; Korean Patent No. 10-0403721, entitled "Lower-alcohol insoluble extraction fraction and polysaccharide substance having activities of reducing hepatotoxicity and eliminating hangover, isolated from *Hovenia dulcis* Thunb., and composition containing the same"; Korean Patent Application No. 10-2002-0079854, entitled "Composition for improving liver function containing a *Hovenia dulcis* Thunb. fruit extract as an active ingredient"; Korean Patent Application No. 10-2003-0027615, entitled "Functional food composition containing as an active ingredient a *Hovenia dulcis* Thunb. fruit extract having excellent effects of improving liver function and eliminating hangover"; and Korean Patent Application No. 10-2013-0088704, entitled "Functional food composition for improving liver function containing Cordyceps militaris extract as active ingredient, and method for preparing the same". However, technology related to a functional food containing a mixture of more effective substances as described in the present invention has not yet been reported.

SUMMARY OF THE INVENTION

It is an object of the present invention to use the functionalities and pharmacological actions of medicinal herbs and to provide a method of preparing a food containing a mixture of highly functional medicinal herb extracts beneficial for the liver, palm oil and grape seed oil, the method comprising the steps of: treating medicinal herbs with hydrogen-rich water; extracting each of the treated medicinal herbs in an extractor; passing the extracts through a packed column; aging the extracts; filtering the aged extracts; adding palm oil to the filtered extracts; aging the mixture in a red clay room; sterilizing the aged mixture by sonication (28 KHz, 30 min); and passing the sterilized mixture through a packed column, and a food prepared by the method.

Accordingly, the present inventor has made extensive efforts to provide a method of preparing a food containing functional substance-containing medicinal herb extracts beneficial for the liver, which can maximize consumer preference based on the functionalities of medicinal herbs and palm oil, and a food prepared thereby. Therefore, the present invention provides a method of preparing a food containing medicinal herb extracts beneficial for the liver, the method comprising the steps of:

(1) washing medicinal herbs, which are *Hovenia dulcis* Thunb., young leaves of *Artemisia scoparia, Pueraria thunbergiana, Curcuma longa, Angelica gigas*, licorice, and cinnamon, with tap water three times, followed by dipping in hydrogen-rich water for 60 minutes and dewatering;

(2) extracting each of the medicinal herbs in an extractor at 121° C. and 1.5 atm for 2 hours to obtain extracts, passing each of the extracts through a packed column (packed sequentially with sponge, chitosan powder and bentonite), followed by aging at 10° C. ° C. for 48 hours and filtration through filter paper (Whatman No. 2);

(3) mixing the filtered extracts with palm oil and grape seed oil at a predetermined ratio to obtain a mixture, and aging the mixture in a red clay room at 30° C. for 24 hours;

(4) sterilizing the aged mixture by sonication at 28 KHz for 30 minutes, followed by passage through a packed column (packed sequentially with a sand layer, a dry grape seed powder layer and a bentonite layer); and (5) packaging the sterilized mixture and making the packaged mixture into a final product.

BRIEF DESCRIPTION OF THE DRAWINGS

FIG. 1 is a flow chart showing a process of preparing a food according to a preferred embodiment of the present invention.

DETAILED DESCRIPTION OF THE INVENTION

Hereinafter, the present invention will be described in detail with reference to FIG. 1.

1. Material Selection and Washing

As raw materials, *Hovenia dulcis* Thunb., young leaves of *Artemisia scoparia, Pueraria thunbergiana, Curcuma longa, Angelica gigas*, licorice, and cinnamon, known as medicinal herbs beneficial for the liver, are washed three times with tap water, and then dipped in 20 liters of hydrogen-rich water (device: NNB Co., Ltd., Korea) for 60 minutes, followed by dewatering.

Each of the raw materials will now be described.

*Hovenia dulcis* Thunb. is a plant belonging to the family. In Korea, *Hovenia dulcis* Thunb. grows mainly in the central and southern regions. The fruit of *Hovenia dulcis* Thunb., known as Hoveniae Semen Cum Fructus, has a soft scent and a sweet taste, and contains components beneficial for the liver. Běncǎo Gāngmù, a Chinese medicinal book, describes as follows: "In the fall, the fruit leaves of *Hovenia dulcis* Thunb. become bulky and have a coral shape. These leaves are used as medicine, and the taste is so sweet that people eat them. The fruits have a medicinal effect that reduces hangover and protects the liver. When *Hovenia dulcis* Thunb. stem slices are added to a jar containing an alcohol, the alcohol becomes watery." In folk remedies, *Hovenia dulcis* Thunb. is used for arthritis, hangover relief, liver diseases, and the like.

For eating, it is known that young leaves of *Hovenia dulcis* Thunb. are eaten after boiling or eaten after pickling.

In Korea, about 40 species of *Artemisia scoparia* grow. Particularly, it grows a lot in sandy beaches and rocks in the central and southern regions of Korea, including Jeju Island. It is a perennial plant and grows to a height of about 60 to 90 cm, and the roots are thick and the upper part of the roots is purple. The leaves are needle-shaped, and the length thereof is 3 to 5 cm. In August to September, upper branches with leaves and flower stems attached are cut and dried in shade for use as medicine. It is known to be effective for various inflammations, urethritis, nervous breakdown, headache, kidney stones, diuresis, bacterial inhibition, expectoration, spasmolytic action, pain relief, jaundice, respiratory disease, anti-inflammation, phlegm, antipyretic action, epilepsy, diarrhea, nervous breakdown, parasitic infection, spinal neuromyositis, and the like. In particular, it is known to be very effective in dissolving kidney and bladder stones.

*Pueraria thunbergiana* is distributed in some regions of Korea, Taiwan, China, etc. The root thereof contains functional substances such as isoflavones, and processed and cooked foods using the same include cold noodles, pork barbecues, and the like. In addition, *Pueraria thunbergiana* is used for hypertension, otitis media, tonic, fever, diarrhea, syrigmus, and the like.

*Curcuma longa* is a perennial plant belonging to the family Zingiberaceae, and is distributed in Korea, China, and the like. The root thereof diketone compound curcumin (yellow crystal component), and has a starch content of about 50%, a crude fiber content of about 5%, an ash content of about 4%, and a water content of about 16%. In addition, it is effective against for hemoptysis, nosebleed, hematuria, gallstones, and as directional nutrients.

*Angelica gigas* is a perennial plant belonging to the family Umbelliferae. It grows to a height of about 1.0 to 2.0 m. The whole stem is purplish, and the root is thick and strongly fragrant. *Angelica gigas* produced in Korea contains volatile essential oil components, such as decurcinol, decursin and the like, fatty acids, vitamins, and the like. It is used as a raw material for oriental medicine or as a food material for boiled vegetables. The effects thereof include inhibition of uterine excitement, promotion of coronary blood flow, anti-inflammatory action, antioxidant activity, and the like.

Licorice is a perennial herbaceous plant belonging to the family Fabaceae, and is native to the Mediterranean and West Asia, and is distributed in Mongolia, Siberia, and the like. It grows mainly in China, the Soviet Union, and Mongolia, and is also cultivated in the lowlands of mountains in Gangwon-do in Korea. It contains a sweet component (glycyrrhizin, glycrrhetinic acid, etc.) content of about 6 to 14%, a sucrose content of about 5%, and a glucose content of about 30%, and contains malic acid. It is used for emulsification of mayonnaise and ice cream, and production of digestion-promoting food, confectionery, cigarettes, and beer.

Cinnamon refers to the stem and branch shell of a cinnamon tree, an evergreen tree belonging to the family Lauraceae. It is native to China, Indonesia and Vietnam. The main components thereof include cinnamic aldehyde, camhene, cineol, linalool, and eugenol, which are essential oils known cinnamon oils. It is used as a raw material for hard-boiled food, seasonings, and the like, and is known to have blood pressure lowering action, platelet aggregation inhibitory action, sedation action, pain relief action, and antipyretic action.

Grape seeds are known to contain polyphenols, resveratrols, linoleic acid, tocopherols, catechins, sterols, and the like, and thus have effects on skin aging prevention, melanin pigment production inhibition, freckle formation prevention, wrinkle formation production, and skin whitening. Meanwhile, products developed using grape seeds include grape seed skin lotion, cleaning lotion, soap, and the like.

Palm oil is an oil extracted from the fruits of a tree belonging to the family Arecaceae. It is cultivated in Southeast Asia and the Pacific Islands, including Philippines, Indonesia, India, Sri Lanka, Papua New Guinea and the like. It contains lauric acid as a main component, and has a saturated fatty (caprylic acid, capric acid, palmitic acid, etc.) content of about 91% and an unsaturated fatty acid content of 9%. It is widely used for food, medicine, industrial applications and religious ceremony purposes. In addition, it is used for various edible products, including chocolate-coated or chocolate-sprayed foods, such as biscuits, cookies, wafers, etc., ice cream, milk substitutes, modified milk powder, etc. In addition, it is also used for cosmetic manufacture and as a raw material for surfactants and biodiesels.

2. Extraction, Aging and Filtration

Each of the medicinal herbs treated with the hydrogen-rich water was extracted in an extractor at 121° C. and 1.5 atm for 2 hours. Each of the extracts was passed through a packed column (packed with sponge, chitosan and bentonite), aged at 10° C. for 48 hours, and filtered through filter paper (Whatman No. 2). Herein, the sponge, chitosan powder and bentonite were purchased from the market.

3. Aging

The extracts obtained in step 2 above were mixed with palm oil at a predetermined weight ratio (20 wt % *Hovenia dulcis* Thunb. extract, 8 wt % young *Artemisia scoparia* leaf extract, 8 wt % *Pueraria thunbergiana* root extract, 5 wt % *Angelica gigas* extract, 6 wt % *Curcuma longa* extract, 2 wt % licorice extract, 1 wt % cinnamon extract, 20 wt % grape seed oil, and 30 wt % palm oil). The mixture was aged in a red clay room at 30° C. for 24 hours. Here, the palm oil used was purchased from the market.

4. Sterilization and Filtration

The mixture aged in step 3 above was sterilized by sonication at 28 KHz for 30 minutes, and then passed through a packed column (packed sequentially with a sand layer, a dry grape seed powder layer, and a bentonite layer). Here, the sonication was performed in a stainless container (28 cm (W)×30 cm (L)×18 cm (H), Tecan, USA) at 28 KHz for 30 minutes.

5. Product

The mixture resulting from step 4 above was packaged and made into a final product.

Hereinafter, a preferred embodiment of the present invention will be described with reference to the accompanying drawing.

(1) Experiment on Change in Color of Final Medicinal Herb Extract Obtained Using Each Treatment The change in the color of the final medicinal herb extract by each treatment was measured, and the results of the measurement are shown in Table 1 below.

TABLE 1

Change in color of final medicinal herb extract obtained using each treatment

| Color | Untreated | Aging | Multi-stage extraction |
|---|---|---|---|
| L (Lightness) | 38.28 | 66.20 | 73.12 |
| A (Redness) | 7.61 | −1.32 | 8.12 |
| B (Yellowness) | 19.21 | 9.19 | 33.18 |

① Color Measurement

Referring to Table 1, 10 ml of each extract was taken and placed in a color measurement cell, and the color was measured three times using a colorimeter (IOR-300, Minolta, Camera Co. Ltd., Osaka, Japan). The measured values were averaged and expressed as L (Lightness), a (Redness), and b (Yellowness) values.

② Results of Measurement of Color Change

Table 1 above shows the results of measuring the change in the color of each final extract obtained by each treatment. As shown therein, the extract obtained using multi-stage extraction showed the highest values as follows: L value=73.12; "a" value=8.12; "b" value=33.18.

(2) Sugar Concentration, pH and Total Polyphenol Content of Final Medicinal Herb Extract Obtained by Each Treatment The sugar concentration, pH and total polyphenol content of the final medicinal herb extract obtained using each treatment were measured, and the measurement results are shown in Table 2 below.

TABLE 2

Sugar concentration, pH and total polyphenol content of final medicinal herb extract obtained using each treatment

|  | Untreated | Aging | Multi-stage extraction |
| --- | --- | --- | --- |
| Sugar content (° Brix) | 5.5 | 4.4 | 3.3 |
| pH | 6.02 | 6.00 | 5.20 |
| Total polyphenol content (ppm) | 550.4 | 650.3 | 700.2 |

① Sugar Content, pH, and Total Polyphenol Content

Total polyphenol content was measured using the Folin & Ciocalteu's method (Amerine et al., 1980). Specifically, 20 ml of methanol was added to 10 g of each sample and centrifuged at room temperature for 24.5 ml of the supernatant was collected, concentrated under reduced pressure, and dissolved in 3 ml of methanol, and the solution was used for measurement of polyphenol content. In a 96-well plate, 1 ml of 2% sodium carbonate solution was added to 50 µl of each extract and allowed to stand for 3 minutes, and then 50 µl of 50% Folin & Ciocalteu's reagent was added thereto. After 30 minutes, the absorbance of the reaction solution at 750 nm was measured. As a reference material, 0.1% gallic acid was used. For the absorbance measurement, Tecan Infinity F-50 ELISA reader was used. For pH measurement, 50 ml of each extract solution was placed in a beaker, and then the pH thereof was measured using a pH meter (HM-30V, Toa, Japan). Measurement of sugar concentration was performed using Poket refractometer PAL-1 (ATAGO Co., Ltd., Japan).

② Results of Measurement

Table 2 above shows the results of measuring the sugar concentration, pH and total polyphenol content of each final extract obtained using each treatment. As shown therein, the sugar concentration was the highest in the untreated group (5.5° Brix), the pH was the highest in the untreated group (6.02), and the total polyphenol content was the highest in the extract obtained using multi-stage extraction (700.2 ppm).

As described above, the present invention provides a method of preparing a food containing medicinal herb extracts beneficial for the liver and palm oil having functionality. The food prepared by the method can satisfy consumer preferences and exhibit high value-added characteristics. Thus, the food is a highly functional food that can secure competitiveness and provide economic benefits.

What is claimed is:

1. A method for preparing a food containing medicinal herb extracts beneficial for the liver, the method comprising the steps of:
   (1) washing medicinal herbs, which are *Hovenia dulcis*, leaves of *Artemisia scoparia, Pueraria thunbergiana, Curcuma longa, Angelica gigas*, licorice, and cinnamon, with tap water three times, followed by dipping in 20 liters of water for 60 minutes and dewatering;
   (2) extracting each of the medicinal herbs, treated with the water, in an extractor at 121° C. and 1.5 atm for 2 hours to obtain extracts, passing each of the extracts through a packed column packed sequentially with sponge, chitosan powder and bentonite, followed by aging at 10° C. for 48 hours and filtration through filter paper;
   (3) mixing the filtered extracts resulting from step (2) with palm oil and grape seed oil to obtain a mixture, and aging the mixture;
   (4) sterilizing the aged mixture by sonication at 28 KHz for 30 minutes, followed by passage through a column packed sequentially with a sand layer, a dry grape seed powder layer and a bentonite layer; and
   (5) packaging the sterilized mixture,
   wherein step (3) comprises mixing, based on the total weight of the mixture, 20 wt % of the *Hovenia dulcis* Thunb. extract, 8 wt % of the *Artemisia scoparia* leaf extract, 8 wt % of the *Pueraria thunbergiana* root extract, 5 wt % of the *Angelica gigas* extract, 6 wt % of the *Curcuma longa* extract, 2 wt % of the licorice extract, 1 wt % of the cinnamon extract, 20 wt % of grape seed oil, and 30 wt % of palm oil, and aging the mixture at 30° C. for 24 hours.

2. A food containing medicinal herb extracts beneficial for the liver, which is prepared by the method of claim 1.

\* \* \* \* \*